(12) United States Patent
Cox

(10) Patent No.: US 11,234,545 B2
(45) Date of Patent: Feb. 1, 2022

(54) URINAL BOTTLE HOLDING APPARATUS

(71) Applicant: Gloria Cox, Riviera Beach, FL (US)

(72) Inventor: Gloria Cox, Riviera Beach, FL (US)

( * ) Notice: Subject to any disclaimer, the term of this patent is extended or adjusted under 35 U.S.C. 154(b) by 0 days.

(21) Appl. No.: 16/915,808

(22) Filed: Jun. 29, 2020

(65) Prior Publication Data
US 2020/0383507 A1 Dec. 10, 2020

Related U.S. Application Data

(60) Provisional application No. 62/840,182, filed on Apr. 29, 2019.

(51) Int. Cl.
*A47G 23/02* (2006.01)
*A61G 9/00* (2006.01)

(52) U.S. Cl.
CPC ......... *A47G 23/0241* (2013.01); *A61G 9/006* (2013.01); *A45F 2200/0583* (2013.01)

(58) Field of Classification Search
CPC ............... A47G 23/0241; A61G 9/006; A45F 2200/0583
See application file for complete search history.

(56) References Cited

U.S. PATENT DOCUMENTS

| | | | | |
|---|---|---|---|---|
| 2,292,055 A | * | 8/1942 | Collins | A61G 9/006 294/145 |
| 3,473,772 A | * | 10/1969 | Nilson | A61G 7/0503 248/214 |
| 3,477,679 A | * | 11/1969 | Lovitz | F16B 45/00 248/213.2 |
| 3,881,677 A | * | 5/1975 | Ihlenfeld | A47C 7/62 248/311.2 |
| 4,825,590 A | * | 5/1989 | Cullinane | A47G 7/044 248/229.16 |
| 5,282,599 A | * | 2/1994 | Arpaia | A47K 11/12 211/88.01 |
| 6,026,519 A | | 2/2000 | Kaluza | |
| 6,484,989 B1 | * | 11/2002 | Connery | A47D 15/00 248/311.2 |
| D468,014 S | | 12/2002 | Girod | |
| 6,592,180 B2 | * | 7/2003 | Combs | B60N 2/28 248/311.2 |

(Continued)

OTHER PUBLICATIONS

Medline EZP—Urinal Holder with Velcro Strap, https://www.exmed.net/medline-ezp-urinal-holder-velcro-strap.

(Continued)

*Primary Examiner* — Anita M King

(57) ABSTRACT

A urinal bottle holding apparatus includes a mounting hook, a urinal bottle holder, and an attachment mechanism so that a urinal bottle can be safely secured adjacent to a patient. The urinal bottle holder includes a rectangular base, an opening, and a support wall. The opening concentrically traverses through the rectangular base so that the urinal bottle can be inserted and secured. The support wall is terminally connected to a bottom edge of the rectangular base thus delineating a stronger platform to integrate a plurality of holder fastening features of the attachment mechanism. The mounting hook is integrated with a plurality of hook fastening features as the mounting hook is frictionally attached to rectangular base and the support wall through the attachment mechanism.

5 Claims, 9 Drawing Sheets

(56) References Cited

U.S. PATENT DOCUMENTS 7,398,951 B1\* 7/2008 Sugalski .............. A61G 7/0503
  248/214
D889,211 S 7/2020 Cox

OTHER PUBLICATIONS

Urinal Holder, https://www.themobilityaidscentre.co.uk/urinal-holder.

\* cited by examiner

URINAL BOTTLE HOLDING APPARATUS

The current application claims a priority to the U.S. provisional patent application Ser. No. 62/840,182 filed on Apr. 29, 2019.

FIELD OF THE INVENTION

The present invention relates generally to liquid container securement devices. More specifically, the present invention is a bottle holder which can be mounted to any suitable objects and allows the bottles to be held in different ways. The present invention is specifically designed for urinal bottles. However, the present invention is not limited to this option, and it may further be adapted for different types of bottles.

BACKGROUND OF THE INVENTION

Urinal bottles are well known in the prior art. Urinal bottles have been used for many years to collect urine specimens for medical testing. Moreover, urinal bottles are often used in the healthcare field to help male and female bedridden patients who find it impossible or difficult to get out of bed during sleep. Urinal bottles allow the patient who has cognition and movement of their arms to toilet independently while lying in the prone position. A plurality of drawbacks is associated with the placement of the urinal bottles. Preferably, the urinal bottles should be placed where the hand of the patient is able to reach it, for example, on the arm of a chair near the patient's bed. However, under some circumstances, the design of the existing urinal bottle holders made it impossible to fit onto the arm of the chair. In other words, the existing urinal bottle holders can only be placed on a fixed location and thus lack flexibility. Moreover, the urinal bottles may vary in shape and/or size, and the existing urinal bottle holders are usually designed to hold the urinal bottle of a particular size and shape. In addition, at nights or in dark places, the patient may find it difficult to find out the location of the urinal bottle. He/she is forced to turn on the lights to get aware of the surrounding, so as to get the urinal bottles. It is an objective of the present invention to solve the abovementioned problems by disclosing a bottle holder that is suitable for securing wide range of objects and for holding different types of urinal bottles. The present invention can be easily mounted to a cylindrical rod that is commonly found within a configuration of a hospital bed, chair, or any other medical related equipment. Furthermore, a phosphorescent material is integrated into the present invention so that the patient can easily identify the location of the present invention without turning on the lights.

SUMMARY OF THE INVENTION

The present invention is a bottle holder specifically designed for holding urinal bottles. The present invention can fit onto a variety of objects such that the urinal bottles can be kept on different places, for example, on the headboards of a bed, the arm of a chair, etc. the present invention also allows urinal bottles with different shapes and/or sizes to be held.

DETAIL DESCRIPTIONS OF THE INVENTION

All illustrations of the drawings are for the purpose of describing selected versions of the present invention and are not intended to limit the scope of the present invention.

Figure 9:
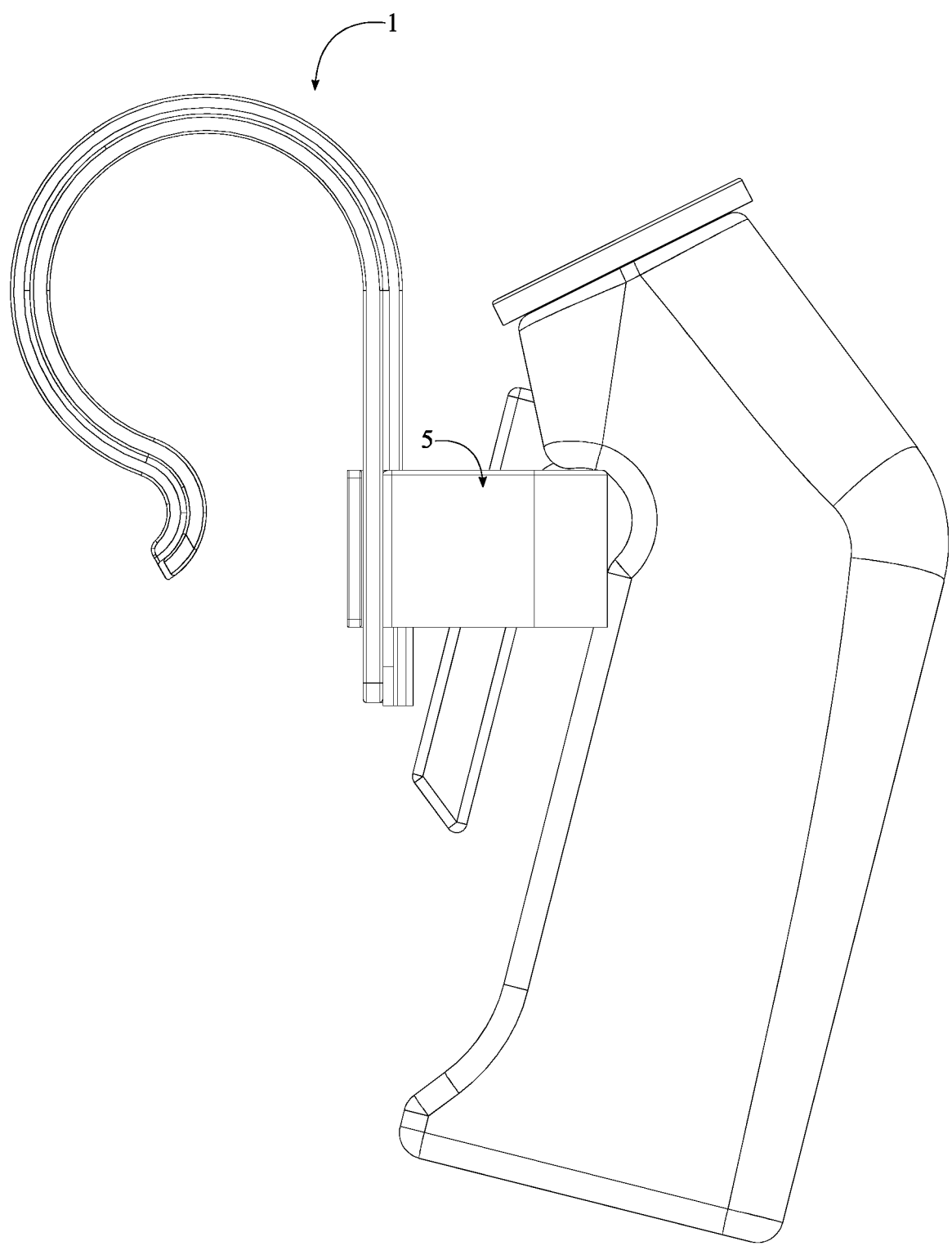
FIG. 9 is a side view showing the placement of urinal bottle within the present invention.

The present invention is a urinal bottle holding apparatus that is specifically designed to hold industry standard urinal bottles. The present invention may be of different shape and/or size to fit any specific urinal bottles and can be removably attached to any cylindrical and/or elongated objects so that users have the ability to choose where to place the urinal bottle. The present invention also offers different ways to hold the urinal bottle, such that the bottle is more readily accessible to the patient as shown in FIG. 9.

Figure 1:
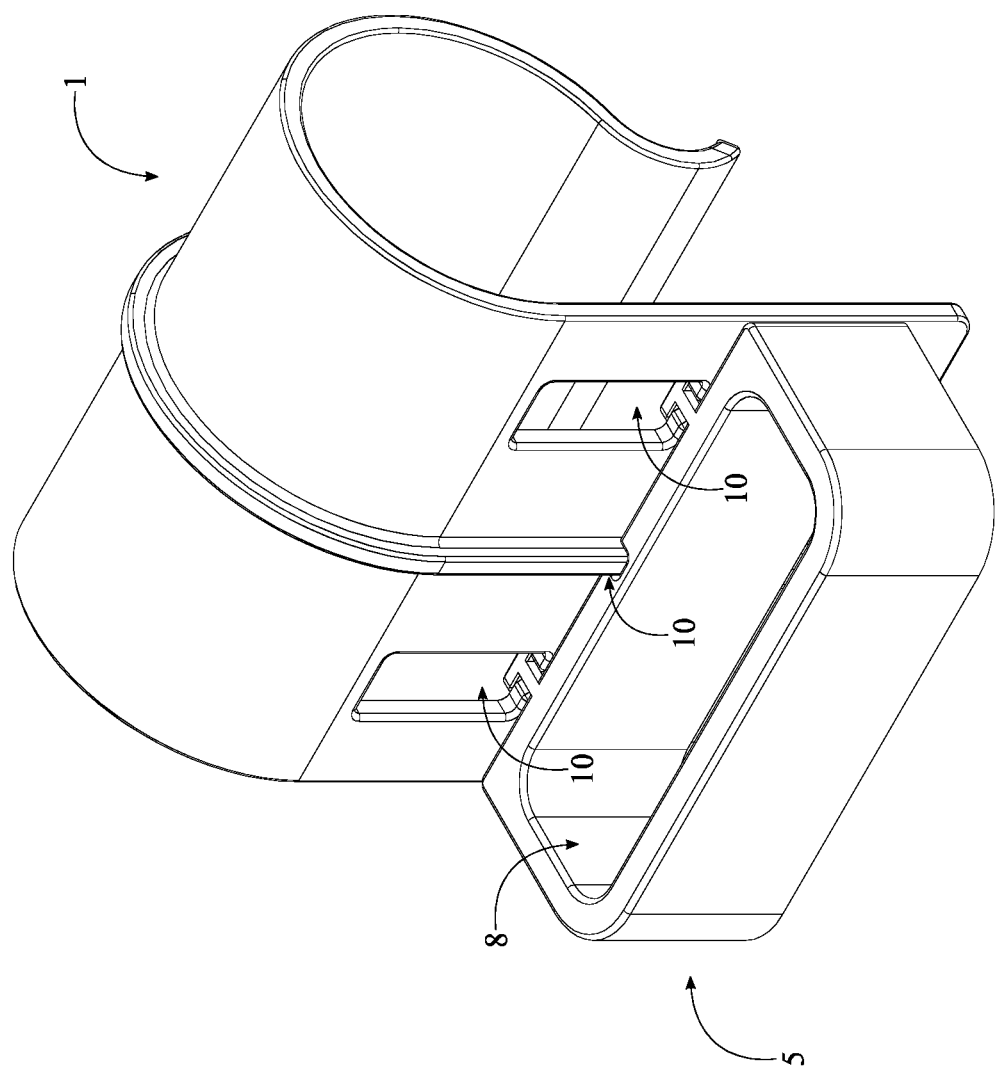
FIG. 1 is a front perspective view of the present invention.
Figure 2:
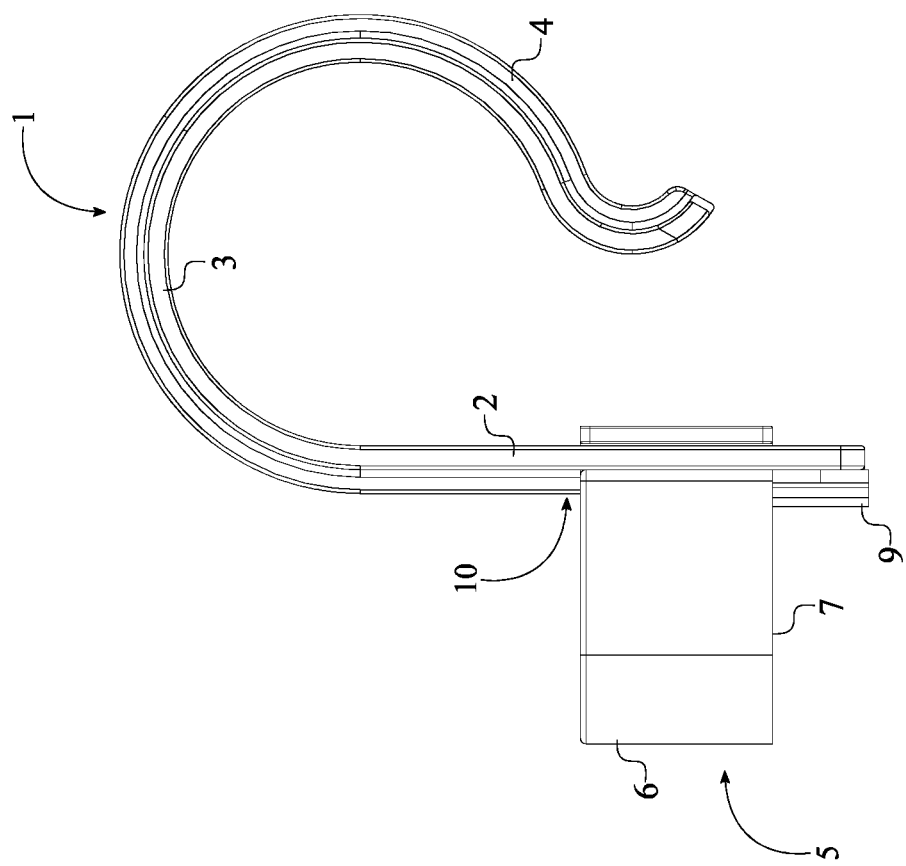
FIG. 2 is a side view of the present invention.
Figure 3:
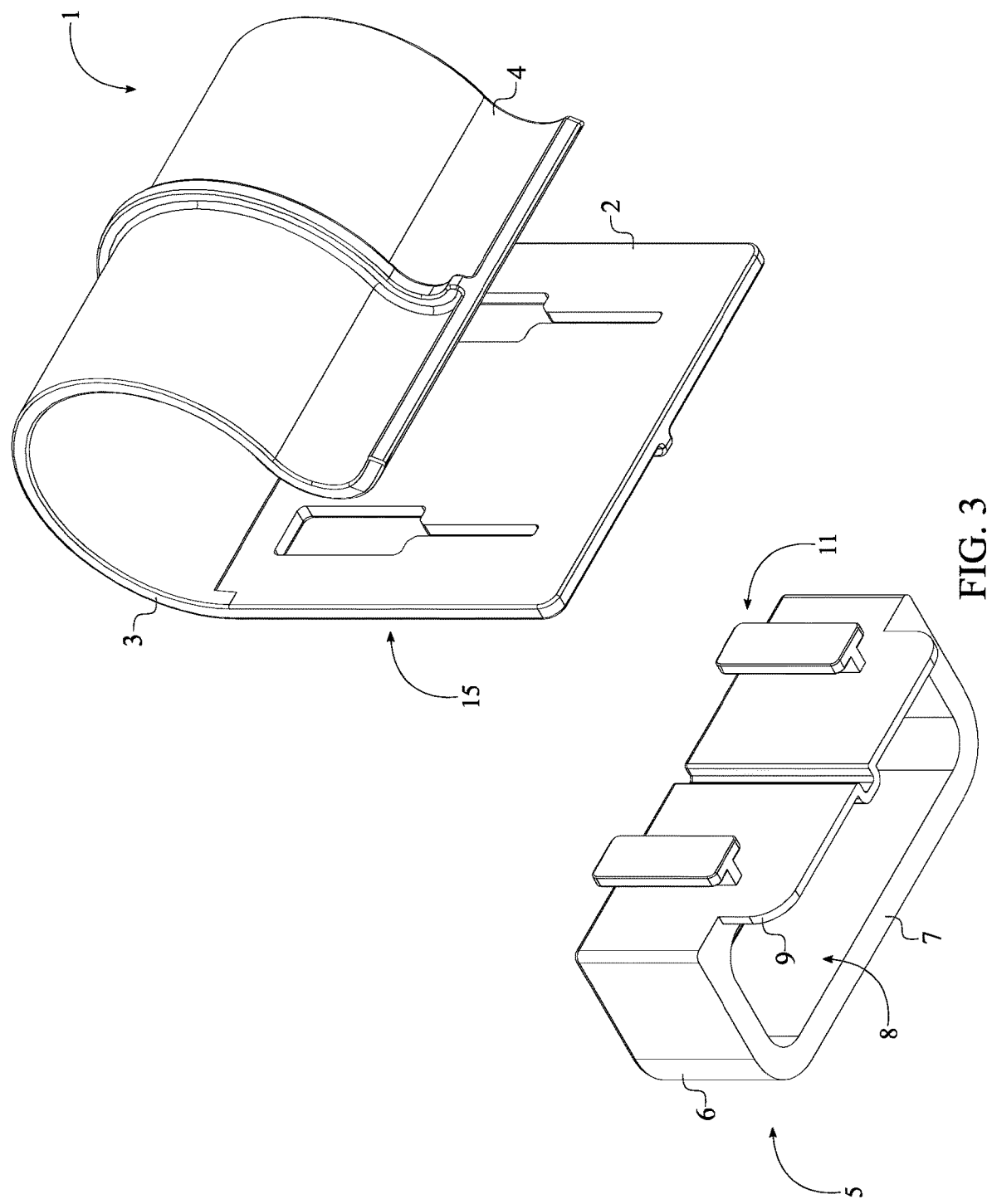
FIG. 3 is a rear exploded and perspective view of the present invention.

The present invention comprises a mounting hook 1, a urinal bottle holder 5, and an attachment mechanism 10 as shown in FIG. 1-3. The urinal bottle holder 5 that secures the industry standard urinal bottles comprises a rectangular base 6, an opening 8, and a support wall 9. The attachment mechanism 10 that slidably attached the mounting hook 1 and the urinal bottle holder 5 comprises a plurality of holder fastening features 11 and a plurality of hook fastening features 15. In reference to a general configuration of the present invention, the opening 8 concentrically traversing through the rectangular base 6 and delineates an empty space to insert the urinal bottle. The support wall 9 is generally shaped into a rectangular body and terminally connected to a bottom edge 7 of the rectangular base 6. Generally, the support wall 9 and a rear section of the rectangular base 6 delineate a rear wall of the urinal bottle holder 5. Furthermore, the support wall 9 functions as an additional structural wall within the present invention in order to optimize the functionality of the attachment mechanism 10. The plurality of holder fastening features 11 is laterally integrated onto the urinal bottle holder 5. The plurality of hook fastening features 15 is laterally integrated onto the mounting hook 1. As a result, the mounting hook 1 can be frictionally attached to rectangular base 6 and the support wall 9 through the plurality of holder fastening features 11 and the plurality of hook fastening features 15.

The mounting hook 1 can be made from any types of flexible material including, but not limited to, rubber, plastic, composite, etc. It should be noted that although the mounting hook 1 is flexible, there is still enough tension in the mounting hook 1 to support the total filled weight of the urinal bottle. In reference to FIG. 2, the mounting hook 1 comprises a straight section 2, an arc section 3, and a curved section 4. More specifically, the straight section 2 and the curved section 4 are oppositely positioned of each other about the arc section 3 thus delineating the general profile of the mounting hook 1. The straight section 2 is terminally connected to the arc section 3 and provides a flat surface area to attach the urinal bottle holder 5. The curved section 4 is terminally connected to the arc section 3, wherein the curved section 4 and the arc section 3 collectively allow the mounting hook 1 to be hung from the cylindrical and/or elongated objects. Furthermore, an access slot is delineated between an end of the curved section 4 and the straight section 2 so that the mounting hook 1 can be inserted around the cylindrical and/or elongated objects through the access slot. Preferably, the length of the access slot is smaller than a chord length of the arc section 3 so that the curved section 4 can be pressed against the cylindrical and/or elongated objects to provide a stable securing position for the mounting hook 1. In some embodiment of the present invention, the access slot can be preferably flexed up to 3 inches. Furthermore, the end of the curved section 4 is oriented away from the straight section 2 thus outwardly expanding the access slot away from the straight section 2 when mounting hook 1 is pressed upon the cylindrical and/or elongated objects. As a result, the mounting hook 1 can be easily flexed outward and engaged around the cylindrical and/or elongated objects.

Figure 4:
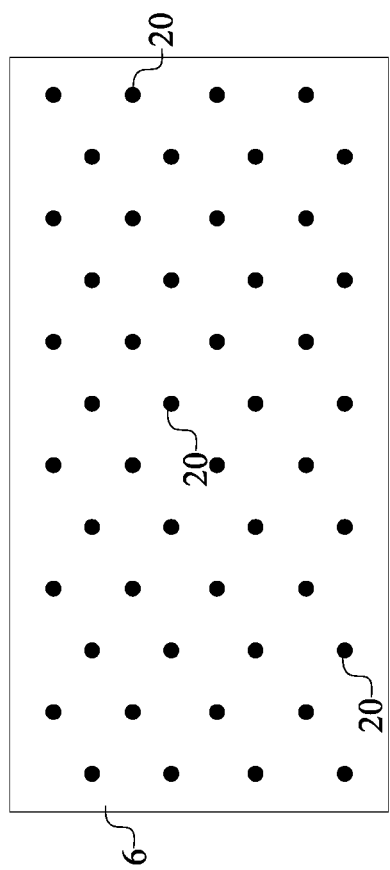
FIG. 4 is a schematic diagram showing the integration of phosphorescent material into the rectangular base of the present invention.
Figure 5:
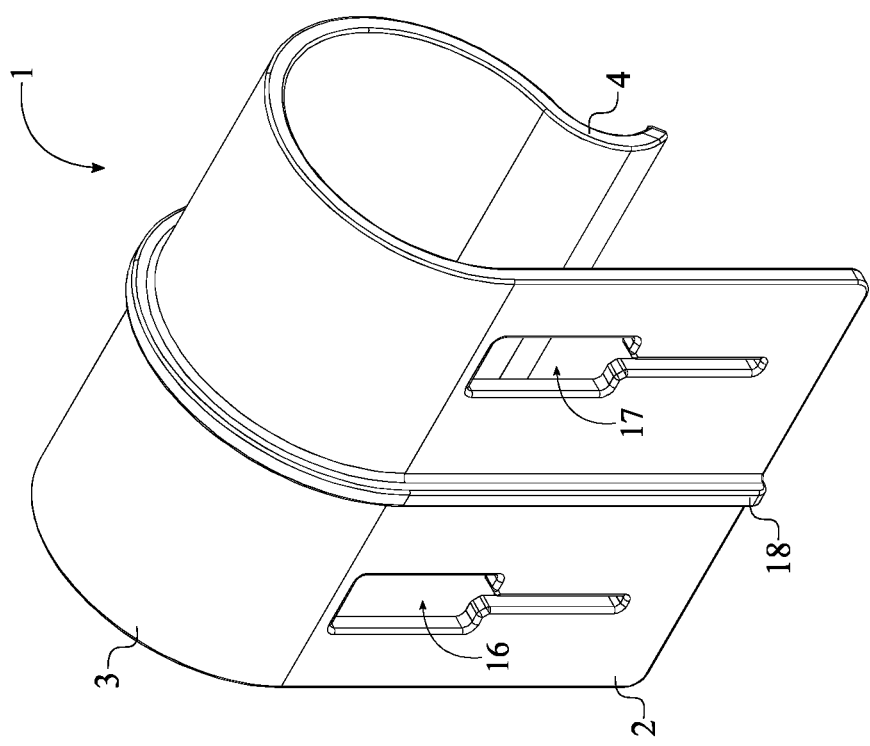
FIG. 5 is a perspective view of the mounting hook of the present invention.
Figure 6:
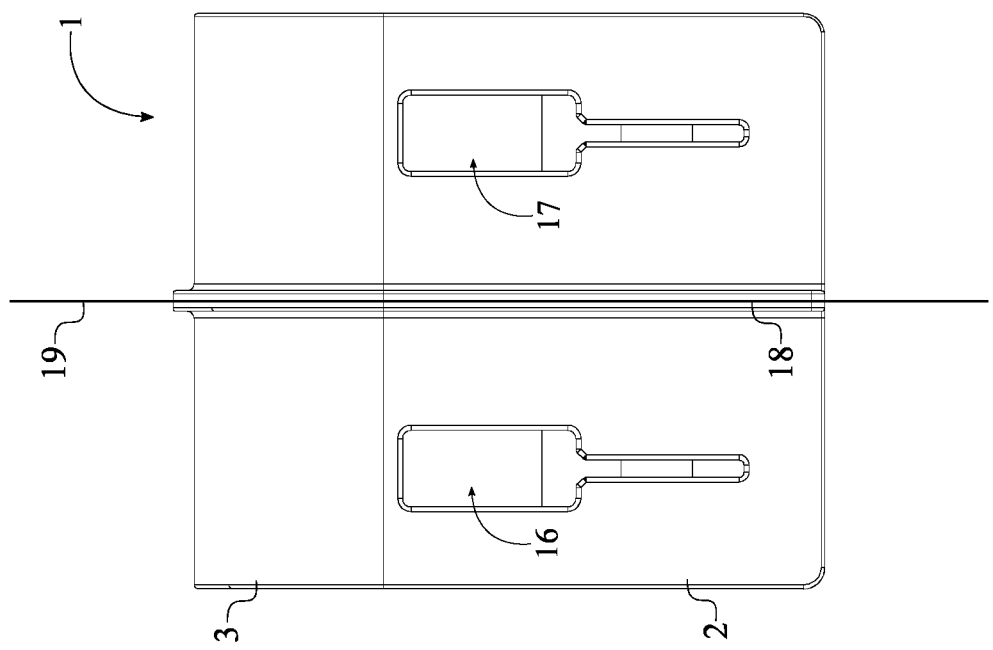
FIG. 6 is a front view of the mounting hook of the present invention.
Figure 7:
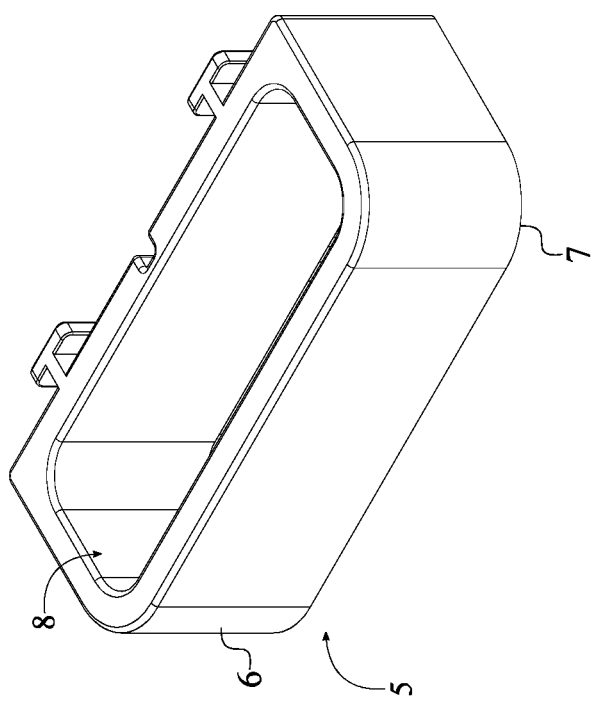
FIG. 7 is a perspective view of the urinal bottle holder of the present invention.
Figure 8:
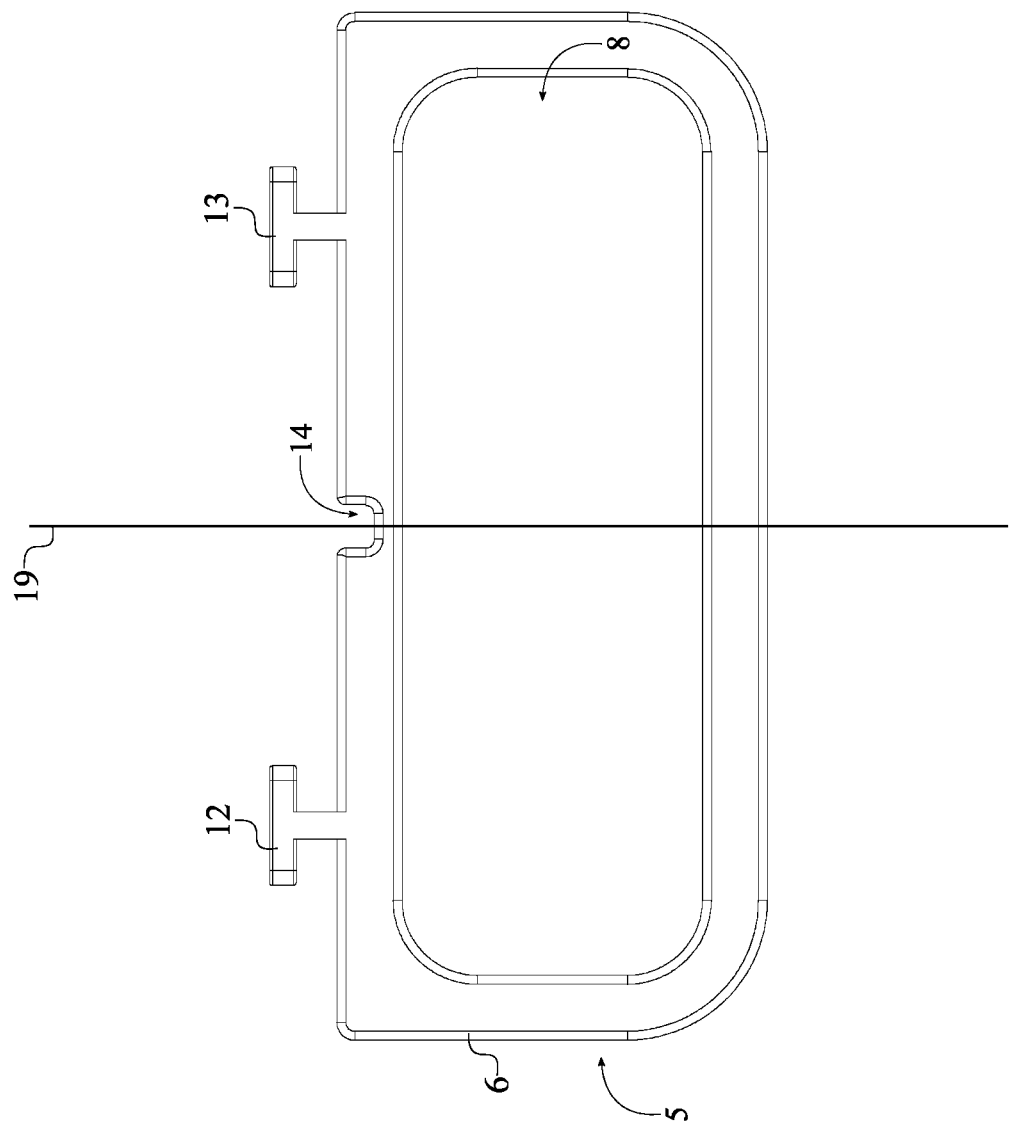
FIG. 8 is a front view of the urinal bottle holder of the present invention.

It should be noted that urinal bottle holder 5 can be made of other shapes including, but not limited, to an ellipse or other regular or irregular polygons as long as the rear wall is delineated for the placement of the plurality of holder fastening features 11. The present invention further comprises a quantity of phosphorescent material 20 that is integrated into the rectangular base 6 as shown in FIG. 4. Resultantly, the quantity of phosphorescent material 20 enables the rectangular base 6 to be glow in the dark thus allowing the users to easily locate the urinal bottle without having to turn on the lights.

In some embodiment of the urinal bottle holder 5, the rectangular base 6 has a U-shaped cross-section and thus forming a cavity from the bottom edge 7 of the rectangular base 6. In this embodiment, a plurality of structural spacers may be provided within the cavity to reinforce the structural integrity of the rectangular base 6.

In reference to FIG. 3 and FIG. 5-8, the plurality of holder fastening features 11 comprises a first tab 12 and a second tab 13. The plurality of hook fastening features 15 comprises a first opening 16 and a second opening 17. The first tab 12 is laterally connected to the rectangular base 6 and the support wall 9. The second tab 13 is laterally connected to the rectangular base 6 and the support wall 9. The first tab 12 and the second tab 13 are externally positioned about the rectangular base 6 and the support wall 9 and symmetrically positioned about a sagittal plane 19 of the present invention. As a result, the first tab 12 and the second tab 13 are able to provide two male fastening features for the urinal bottle holder 5. The first opening 16 traverses through the straight section 2. The second opening 17 traverses through the straight section 2. The first opening 16 and the second opening 17 are symmetrically positioned about the sagittal plane 19, so that the first opening 16 is able to align with the first tab 12 and the second opening 17 is able to align with the second tab 13. In order to complete the attachment points between the mounting hook 1 and the urinal bottle holder 5, the first tab 12 is slidably engaged within the first opening 16 and the second tab 13 is slidably engaged within the second opening 17.

More specifically, the first tab 12 and the second tab 13 each comprises a narrow section and a wider section. The narrow section is connected along the rectangular base 6 and the support wall 9. The wider section is symmetrically connected along the narrow section and positioned opposite of the support wall 9. In other words, the narrow section and the wider section delineate a T-shaped profile for the first tab 12 and the second tab 13 as the bottom end of the T-shaped profile is connected along the rectangular base 6 and the support wall 9. The first opening 16 and the second opening 17 each comprises a wider channel and a narrow channel. The wider channel and the narrow channel are adjacently connected to each other, wherein the narrow channel is oriented toward an end of straight section 2. In other words, the narrow channel and the wider channel delineate a T-shaped profile for the first opening 16 and the second opening 17 as the bottom end of the T-shaped profile is oriented toward the end of the straight section 2.

In order to attach the mounting hook 1 and the urinal bottle holder 5 together, the wider section is first aligned with the wider channel so that the wider section can be inserted through. Once the wider section is inserted through the wider channel, the rectangular base 6 is pressed downward toward the end of the straight section 2. Resultantly, the narrow section engages with the narrow channel and secures the urinal bottle holder 5 to the mounting hook 1. Since the wider section is larger than the narrow channel, the urinal bottle holder 5 does not disengage from the mounting hook 1.

In reference to FIG. 5-8, the plurality of holder fastening features 11 further comprises an alignment cavity 14. The plurality of hook fastening features 15 further comprises an alignment rail 18. The alignment cavity 14 laterally traverses into the rectangular base 6 and the support wall 9 and positioned along the sagittal plane 19. The alignment rail 18 that provides additional stiffness to the mounting hook 1 is laterally connected along the mounting hook 1 and positioned along the sagittal plane 19. When the mounting hook 1 and the urinal bottle holder 5 are attached to each other, the alignment cavity 14 is engaged around the alignment rail 18 thus aligning the first tab 12 with the first opening 16 and the second tab 13 with the second opening 17.

Although the invention has been explained in relation to its preferred embodiment, it is to be understood that many other possible modifications and variations can be made without departing from the spirit and scope of the invention as hereinafter claimed.

What is claimed is:

1. A urinal bottle holding apparatus comprising:
   a mounting hook;
   a urinal bottle holder;
   an attachment mechanism;
   a sagittal plane;
   the urinal bottle holder comprising a rectangular base, an opening, and a support wall;
   the attachment mechanism comprising a plurality of holder fastening features and a plurality of hook fastening features;
   the opening concentrically traversing through the rectangular base;
   the support wall being terminally connected to a bottom edge of the rectangular base;
   the plurality of holder fastening features being laterally integrated onto the urinal bottle holder;
   the plurality of hook fastening features being laterally integrated onto the mounting hook;
   the mounting hook being frictionally attached to rectangular base and the support wall through the plurality of holder fastening features and the plurality of hook fastening features;
   the plurality of holder fastening features comprising an alignment cavity;

the plurality of hook fastening features comprising an alignment rail;
the alignment cavity traversing into the rectangular base and the support wall;
the alignment cavity being positioned along the sagittal plane;
the alignment rail being laterally connected along the mounting hook;
the alignment rail being positioned along the sagittal plane; and
the alignment cavity being engaged around the alignment rail.

2. The urinal bottle holding apparatus as claimed in claim 1, wherein the mounting hook is flexible.

3. The urinal bottle holding apparatus as claimed in claim 1 comprising:
the mounting hook comprising a straight section, an arc section, and a curved section;
the straight section and the curved section being oppositely positioned of each other about the arc section;
the straight section being terminally connected to the arc section; and
the curved section being terminally connected to the arc section.

4. The urinal bottle holding apparatus as claimed in claim 1 comprising:
a quantity of phosphorescent material; and
the quantity of phosphorescent material being integrated into the rectangular base.

5. The urinal bottle holding apparatus as claimed in claim 1 comprising:
the plurality of holder fastening features further comprising a first tab and a second tab;
the plurality of hook fastening features further comprising a first opening and a second opening;
the first tab being laterally connected to the rectangular base and the support wall;
the second tab being laterally connected to the rectangular base and the support wall;
the first tab and the second tab being externally positioned about the rectangular base and the support wall;
the first tab and the second tab being symmetrically positioned about the sagittal plane;
the first opening traversing through the straight section;
the second opening traversing through the straight section;
the first opening and the second opening being symmetrically positioned about the sagittal plane;
the first tab being slidably engaged within the first opening; and
the second tab being slidably engaged within the second opening.

* * * * *